United States Patent
Tijm et al.

(10) Patent No.: US 8,921,431 B2
(45) Date of Patent: Dec. 30, 2014

(54) METHODS FOR IMPROVING HIGHER ALCOHOL YIELDS FROM SYNGAS BY ALTERING FLOW REGIMES WITHIN A REACTOR

(71) Applicants: Peter J. Tijm, Glenwood Springs, CO (US); Faisal Baksh, Manama (BH)

(72) Inventors: Peter J. Tijm, Glenwood Springs, CO (US); Faisal Baksh, Manama (BH)

(73) Assignee: Standard Alcohol Company of America, Inc., Denver, CO (US)

( * ) Notice: Subject to any disclaimer, the term of this patent is extended or adjusted under 35 U.S.C. 154(b) by 0 days.

(21) Appl. No.: 13/777,796

(22) Filed: Feb. 26, 2013

(65) Prior Publication Data

US 2014/0066525 A1    Mar. 6, 2014

Related U.S. Application Data

(60) Provisional application No. 61/604,634, filed on Feb. 29, 2012.

(51) Int. Cl.
*C07C 27/06* (2006.01)
*C07C 29/151* (2006.01)
*C07C 29/74* (2006.01)
*C07C 1/04* (2006.01)

(52) U.S. Cl.
CPC ........... *C07C 29/1514* (2013.01); *C07C 1/0485* (2013.01)
USPC ............................ 518/700; 568/840; 568/913

(58) Field of Classification Search
USPC .................................. 518/700; 568/840, 913
See application file for complete search history.

(56) References Cited

U.S. PATENT DOCUMENTS

| | | |
|---|---|---|
| 2,128,910 A | 9/1938 | Bludworth |
| 3,822,119 A | 7/1974 | Frech |
| 3,968,999 A | 7/1976 | Keller |
| 4,018,293 A | 4/1977 | Keller |
| 4,030,893 A | 6/1977 | Keller |
| 4,045,092 A | 8/1977 | Keller |
| 4,089,657 A | 5/1978 | Keller |
| 4,097,217 A | 6/1978 | Keller |
| 4,146,366 A | 3/1979 | Keller |
| 4,192,651 A | 3/1980 | Keller |
| 4,218,516 A | 8/1980 | Meyer et al. |

(Continued)

FOREIGN PATENT DOCUMENTS

CN        1089299        7/1994

OTHER PUBLICATIONS

Qin, Z.; Liu, J.; Wang, J. "Solvent Effects on higher alcohols synthesis under supercritical conditions: a thermodynamic consideration" Fuel Processing Technology 85 (2004) p. 1175-1192.*

(Continued)

*Primary Examiner* — Jafar Parsa
*Assistant Examiner* — Amy C Bonaparte
(74) *Attorney, Agent, or Firm* — Geoffrey A. Mantooth

(57) ABSTRACT

Mixed alcohols are produced from syngas. The syngas is provided to a catalyst in a reactor at selected temperatures and pressures. Reactive products, including mixed alcohols, are removed from the reactor. Non-reactive components are removed from the mixed alcohols of their reaction products. At least part of the non-reactive components are reintroduced in the reactor along with syngas. The non-reactive components are a solvent or a supercritical fluid. The nonreactive components can be reintroduced into the reactor with reactive components such as methanol or $CO_2$.

11 Claims, 6 Drawing Sheets

(56) References Cited

U.S. PATENT DOCUMENTS

| | | | |
|---|---|---|---|
| 4,298,354 | A | 11/1981 | Hardman et al. |
| 4,357,146 | A | 11/1982 | Heeren |
| 4,366,032 | A | 12/1982 | Mikitenko et al. |
| 4,384,872 | A | 5/1983 | Kester et al. |
| 4,479,807 | A | 10/1984 | Rebandt |
| 4,533,508 | A | 8/1985 | Stevens |
| 4,561,861 | A | 12/1985 | Davis et al. |
| 4,675,344 | A | 6/1987 | Conway et al. |
| 4,705,532 | A | 11/1987 | Mazanec et al. |
| 4,752,622 | A | 6/1988 | Stevens |
| 4,752,623 | A | 6/1988 | Stevens |
| 4,762,858 | A | 8/1988 | Hucul et al. |
| 4,825,013 | A | 4/1989 | Quarderer et al. |
| 4,831,060 | A | 5/1989 | Stevens et al. |
| 4,871,397 | A | 10/1989 | Stevens |
| 4,882,360 | A | 11/1989 | Stevens |
| 4,895,662 | A | 1/1990 | Stevens |
| 4,953,479 | A | 9/1990 | Keller et al. |
| RE33,562 | E | 4/1991 | Badger |
| 5,045,087 | A | 9/1991 | Keller |
| 5,288,393 | A | 2/1994 | Jessup et al. |
| 5,559,275 | A | 9/1996 | Barger |
| 5,653,886 | A | 8/1997 | Kerr et al. |
| 5,662,455 | A | 9/1997 | Iwata et al. |
| 5,720,784 | A | 2/1998 | Killick et al. |
| 5,837,126 | A | 11/1998 | Jessup et al. |
| 6,030,521 | A | 2/2000 | Jessup et al. |
| 6,039,772 | A | 3/2000 | Orr |
| 6,129,773 | A | 10/2000 | Killick et al. |
| 6,858,048 | B1 | 2/2005 | Jimeson et al. |
| 7,559,961 | B2 | 7/2009 | Jimeson et al. |
| 7,923,405 | B2 | 4/2011 | Kharas et al. |
| 8,277,522 | B2 | 10/2012 | Jimeson et al. |
| 8,299,132 | B2 | 10/2012 | Gracey et al. |
| 8,318,986 | B2 | 11/2012 | Alsum et al. |
| 8,329,960 | B2 | 12/2012 | Gracey et al. |
| 8,354,357 | B2 | 1/2013 | Kharas et al. |
| 2002/0077374 | A1 | 6/2002 | Jackson et al. |
| 2007/0259972 | A1 | 11/2007 | Lattner et al. |
| 2008/0051476 | A1* | 2/2008 | Russell et al. ............... 518/718 |
| 2008/0178784 | A1 | 7/2008 | Farone |
| 2008/0283411 | A1 | 11/2008 | Eastman et al. |
| 2010/0024288 | A1 | 2/2010 | Jimeson et al. |
| 2010/0069515 | A1 | 3/2010 | Tirtowidjojo et al. |
| 2011/0178186 | A1 | 7/2011 | Oh et al. |
| 2011/0201700 | A1 | 8/2011 | Lucas et al. |

OTHER PUBLICATIONS

International Search Report, 2 pages, and Written Opinion, 5 pages, of PCT Patent Application No. PCT/US2013/027986 filed Feb. 24, 2013; Applicant: Standard Alcohol Company of America, Inc.

"The Economical Production of Alcohol Fuels From Coal-Derived Synthesis Gas", Quarterly Technical Progress Report No. 18, W. Virginia Univ. Research Corp., Apr. 1996, 15 pgs.

"Dow Develops Catalytic Method to Produce Higher Mixed Alcohols", Technology, Nov. 12, 1984, pp. 29-30.

Mixed Alcohols From Synthesis Gas, Dow Chemical, M.J. Mintz and G.J. Quarderer, pp. 1-21.

"Elevation of Synthesis Gas Based High Octane Oxygenates", (The Mised Alcohols Option), Absel Elsaway and David Gray, Nov. 1988, pp. 119-136.

Letter with enclosures from Lurgi GmbH to Wayne Kreis of the Texas Methanol Corp., dated Jan. 19, 1987, ref: Octamix-Sample Shipment of Jan. 17, 1987, Frankfurt, Germany, 3 pgs.

* cited by examiner

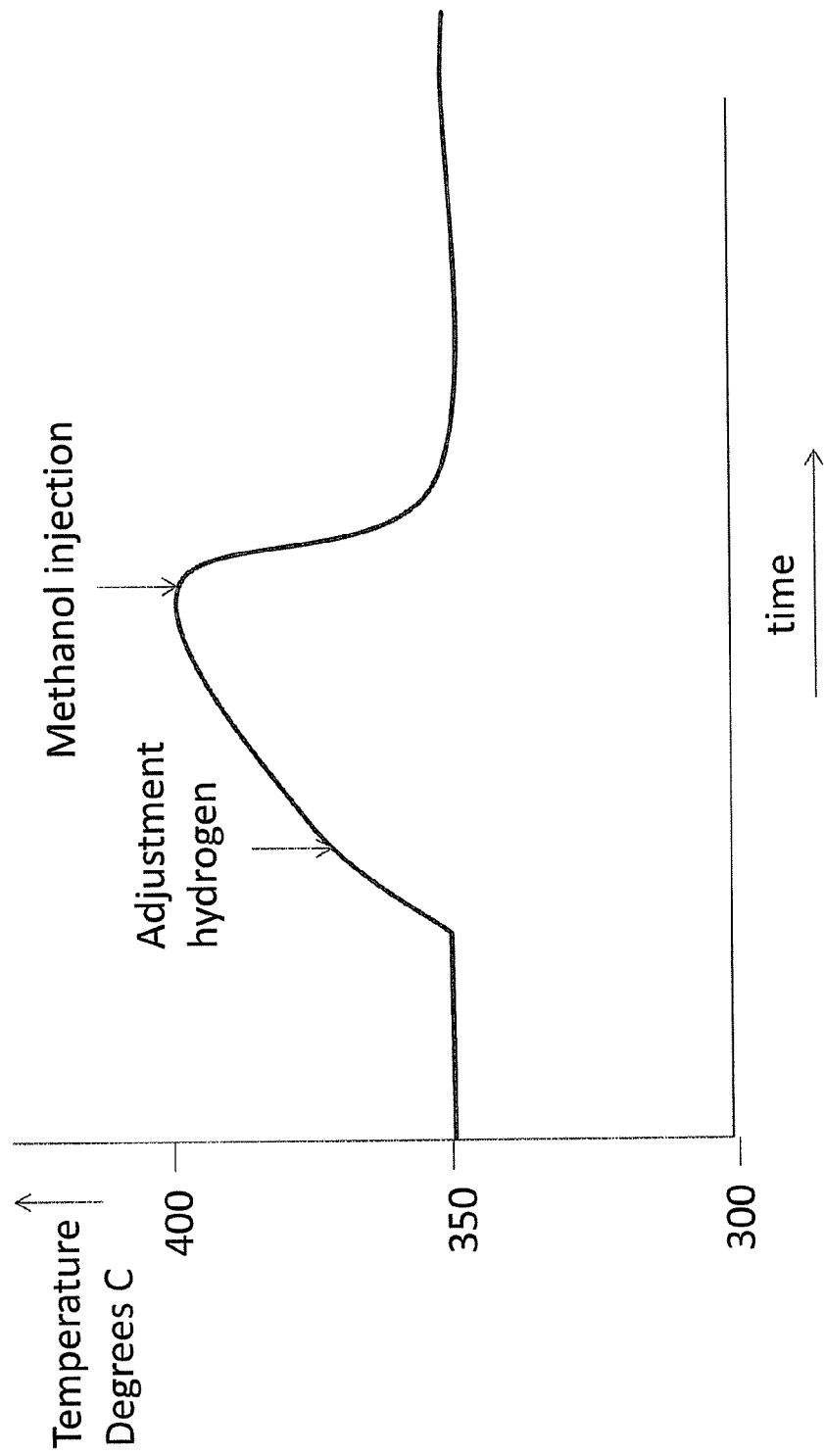
Fig. 6. Temperature profile in MAS reactor, followed by regaining control through methanol injection

METHODS FOR IMPROVING HIGHER ALCOHOL YIELDS FROM SYNGAS BY ALTERING FLOW REGIMES WITHIN A REACTOR

This application claims the benefit of U.S. provisional patent application Ser. No. 61/604,634, filed Feb. 29, 2012.

FIELD OF THE INVENTION

The present invention relates to methods for mixed alcohol synthesis from syngas.

BACKGROUND OF THE INVENTION

Synthesis gas, or syngas, is made up of hydrogen ($H_2$) and carbon monoxide (CO) and may contain some carbon dioxide ($CO_2$) (and may contain other components as well). Syngas is used to produce products such as synthetic natural gas, methanol, ammonia, hydrogen, oxo-alcohols, and FT chemicals like gasoline, diesel, lubes etc. Syngas is available from a variety of sources, such as reforming natural gas, coal-bed gas or naphtha, from the gasification of coal, biomass, carbon rich materials, municipal wastes, etc.

In addition to producing methanol, syngas can be used to produce mixed alcohols in a process generally referred to as Mixed Alcohol Synthesis (MAS). The mixed alcohols include methanol, ethanol, and the higher alcohols (for example propanol, butanol, etc.)

In the prior art, MAS encounters a number of problems. One problem is temperature control especially at higher levels of production required for commercial operation. Syngas is introduced into a reactor under controlled temperatures and pressures and contacted with a catalyst in a gas-solid interface. The reaction is very exothermic. The catalyst is packed into tubes in the reactor and the syngas passes through the tubes. Coolant in the form of water, oil or molten salt surrounds the tubes. Unfortunately, the reaction is unstable and the temperatures may rise locally to unacceptable levels. At such temperature levels the catalyst performs reactions other than making higher alcohol: it performs methanation, i.e. combines CO and $H_2$ in the form of the undesirable product methane ($CH_4$) in a reaction which is even more exothermic and can lead to temperature run-away. As a result, what works in a laboratory or on a small scale, where the catalyst is most frequently diluted with inert material, encounters great difficulty in larger scale reactors which are necessary for commercial development and production.

In the prior art, attempts have been made to stabilize the reaction by modifying the reactor itself. For example, the tubes have been modified. Such reactor modifications are expensive and have not proven to work satisfactorily.

Another problem with the prior art is the relatively high yield of methanol ($C_1$, which means one carbon atom) and the low yield of higher alcohols such as $C_2$ ethanol, $C_3$ propanol, etc. Higher alcohols are desired fuel sources because their energy density is greater. The relatively high production of methanol is also the effect of the heat of reaction. The growth of higher alcohols contributes to the Fischer-Tropsch related chain growth mechanism. This chain growth is negatively influenced by higher local temperatures through increased molecular intrinsic energy, allowing the alcohol molecule to "jump off" the catalyst prematurely.

Still another problem with the prior art is the intolerance of variations of the syngas. The syngas is provided at a certain ratio of $H_2$:CO. If this ratio varies, the reaction is adversely affected, especially under local high H2 concentrations as H2 is a chain terminator. Hence, this leads to production of (undesirable) lower alcohols.

Likewise, the prior art suffers from inflexibility in changing the mix of alcohols that are produced. For example, if a certain mix of higher alcohols is desired, then the prior art is generally incapable of such results.

SUMMARY OF THE INVENTION

A method produces alcohols from syngas. A catalyst is provided in a mixed alcohol synthesis reactor. Syngas is provided to the reactor at temperatures of 240-400 degrees C. and pressures of 500-2500 psi, wherein reaction products are formed. The reaction products comprise mixed alcohols. At least a portion of the reaction products are removed from the reactor. Non-reactive components are removed from the mixed alcohols of the reaction products. At least part of the non-reactive components are reintroduced into the reactor and interacted the syngas and the catalyst in a wet mode so as to produce further reaction products that comprise mixed alcohols.

In accordance with one aspect, the reintroduced non-reactive components comprise a solvent for the mixed alcohols, wherein the solvent alters the flow regime within the reactor and improves heat transfer and mass transfer.

In accordance with another aspect, the solvents are taken from the group consisting of decane, cetane, decahydronapthlene and C11-C20 hydrocarbons.

In accordance with still another aspect, the step of removing non-reactive components from the mixed alcohols further comprises the step of using a vapor-liquid-liquid separator.

In accordance with another aspect, the reintroduced non-reactive components comprise a supercritical fluid that is liquid at room conditions and supercritical in the reactor.

In accordance with another aspect, the supercritical fluid is taken from the group consisting of hexane, heptane, acetone, acetonitrile.

In accordance with another aspect, the step of removing non-reactive components from the mixed alcohols further comprises using a first vapor-liquid separator to separate unreacted syngas, CO2 and the non-reactive components from the mixed alcohols, and then a second separator to separate the non-reactive components from the unreacted syngas and CO2.

BRIEF DESCRIPTION OF THE DRAWINGS

FIG. 6 is a temperature profile of MAS reactor under temperature run-away, followed by recovery of control through methanol injection.

DESCRIPTION OF THE PREFERRED EMBODIMENTS

The method described herein introduces syngas into a reactor and contacts the syngas with a catalyst through a gasliquid-solid phase or a gas-supercritical-solid phase. In addition to the syngas, a suitable solvent or liquid is introduced, which solvent or liquid may or may not participate in the MAS reaction.

The method stabilizes the inherently unstable reaction and allows the reaction to proceed at a commercial scale. The method obtains greater yields of total alcohols and in particular greater yields of higher alcohols (such as $C_2$, or ethanol, and greater) and is able to target a specific alcohol cut for synthesis within the product crude of $C_1$-$C_9$ alcohols. Furthermore, different syngas sources, with different $H_2$:CO ratios can be used, because the optimal ratio can be altered.

Figure 1:
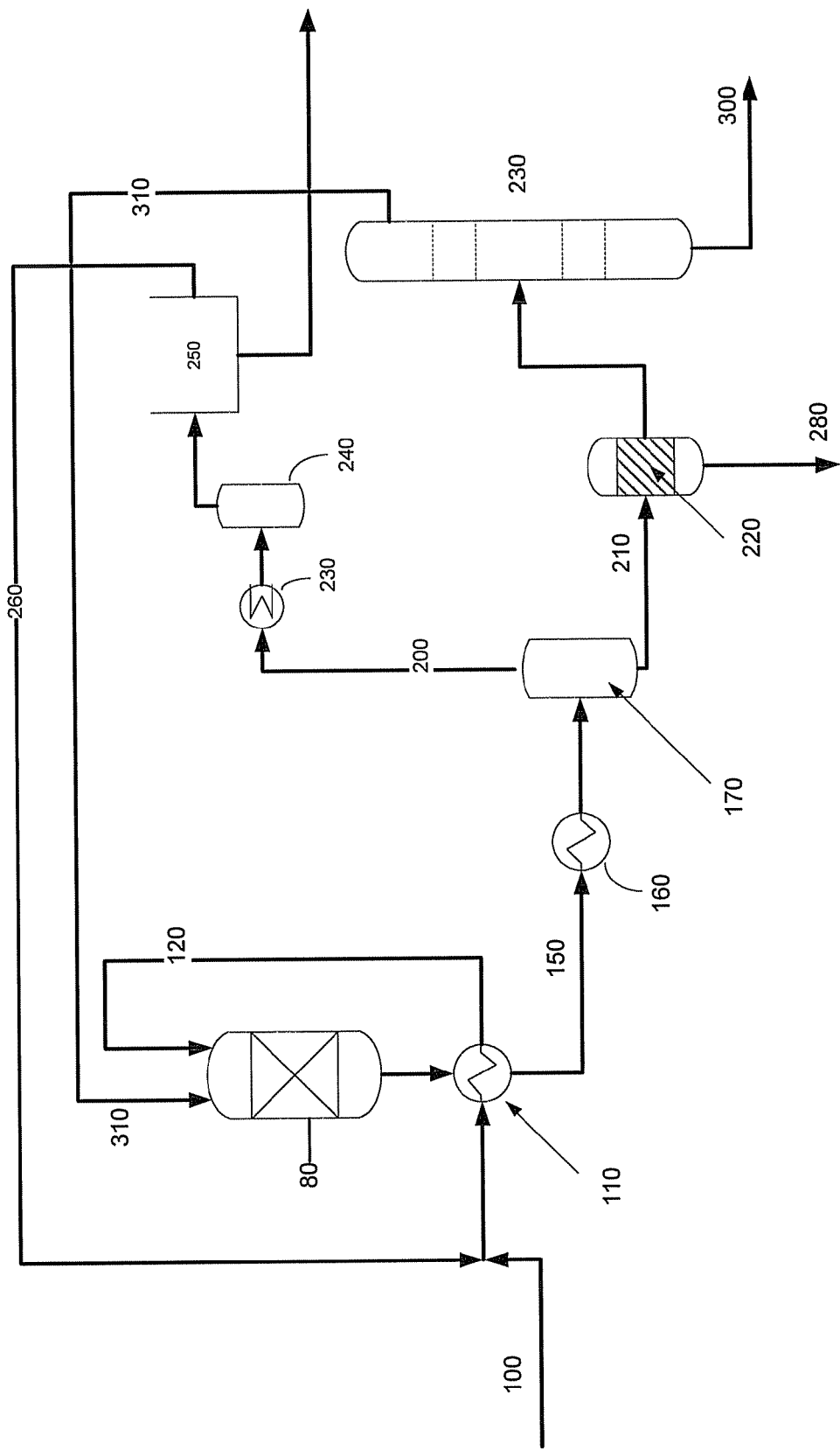
FIG. 1 is a schematic view of a system for practicing the MAS process, in accordance with one embodiment.
Figure 2:
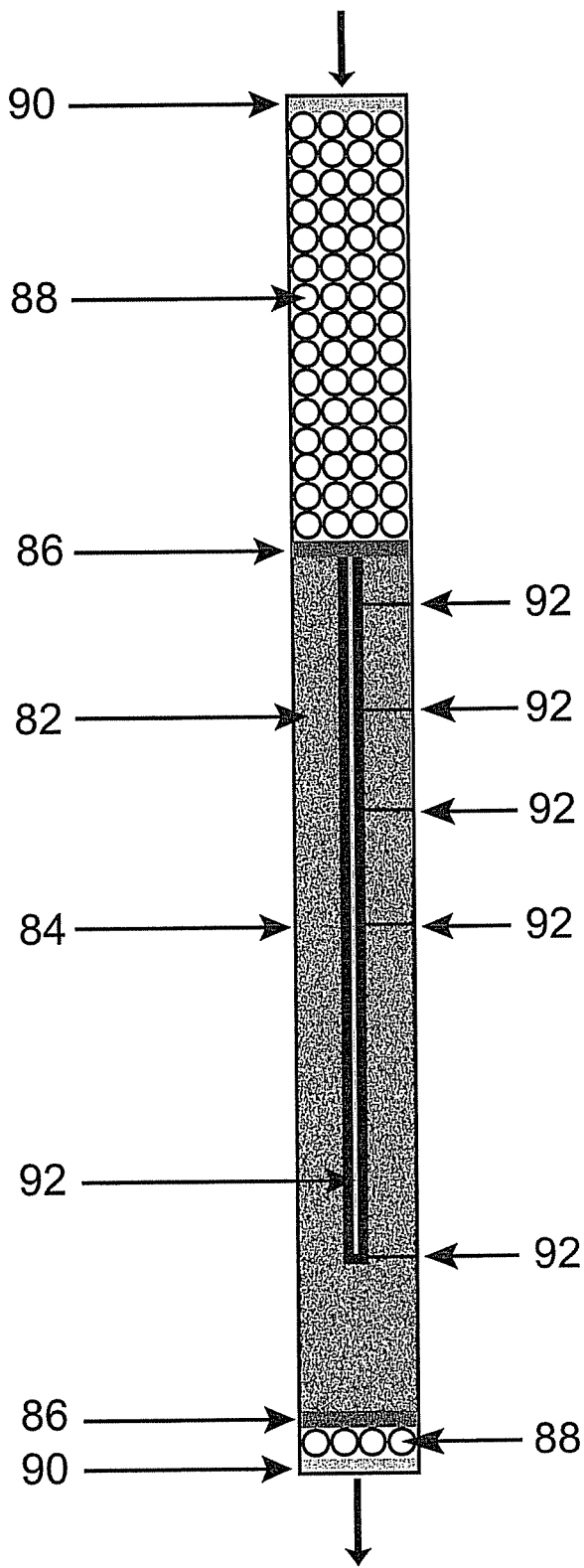
FIG. 2 is a longitudinal cross-sectional view of a tube in the reactor.

FIG. 1 shows the system 70 for the MAS process, in accordance with one embodiment. In the description, like reference numbers among the figures mean like components. The system has a reactor 80. The reactor can be one of various types, such as a fixed bed reactor or a fluid bed reactor. In the preferred embodiment, the reactor is a fixed bed reactor, with tubes extending through a shell. The reactor has plural tubes 82 inside of a shell. Referring to FIG. 2, each tube 82 contains a catalyst 84 within the segment of the tube length. The ends of the catalyst 84 are capped with quartz wool 86, glass beads 88 and sintered metal mesh 90. One or more thermocouples 92 can be provided inside the tube to monitor temperature. As shown in FIG. 2, fluid, including the syngas, flows through the tube 82 from top to bottom. A coolant, such as water, is provided in the shell surrounding the tubes 82.

During initial startup, steam is injected into the shell so as to bring the tubes to operational temperature. Once the reaction begins, the reaction is exothermic and steam injection is no longer needed. Instead, the reaction produces heat, heating the water, or other coolant, in the shell. This in turn produces steam which can be used for a variety of purposes.

The catalyst can be any one of the catalysts known in the field of mixed alcohol synthesis. The following patents discussing catalyst compositions for MAS process, are a few examples and not a complete list, of catalysts which can be used: Dow, U.S. Pat. Nos. 4,825,013, 4,752,622, 4,752,623, 4,675,344, 4,831,060 and 4,882,360; IFP, U.S. Pat. Nos. 5,109,027, 4,346,179, 4,791,141, 4,780,481 and 4,291,126; Union Carbide, U.S. Pat. Nos. 4,992,298 and 4,943,551; Exxon, U.S. Pat. No. 6,680,272; and Snamprogetti, U.S. Pat. Nos. 4,481,012, 4,513,100 and 5,767,166.

The catalyst composition may comprise:
1. Metallic catalytic components:
   a. Main catalytic metal comprising an element from group VIB, typically Cr, Mo or W, most preferentially Mo.
      OR Main catalytic metals from group VIB, preferentially Cr, and another from group IB, typically Cu, Ag, Au, most preferably Cu.
   b. Co-catalytic metals comprising elements from group VIIIB, which essentially act as co-promoters, e.g. Fe, Co, Ni, Ru, Rh, Pd etc. The amount of co-catalytic metal in relation to main catalytic metal varies, typically between 10-60% of main catalytic metal, more preferentially 25-50%.
   c. Compounding elements from sulfur, phosphorous, nitrogen, oxygen or carbon; which combine with at least the main catalytic metal, and preferentially also with the co-catalytic metals to form sulfides, phosphides, nitrides, oxides or carbides.
   d. A promoter, from either group IA, IIA or IIIB, typically Li, Na, K, Cs, Ca, La, preferentially potassium, used for developing desired alcohol selectivity. Its inclusion can also either be during precipitation stages or as the final stage. Amount of promoter metal in relation to catalytic metal (a+b) can vary, typically between 0.5-30.0% of catalytic metal (a+b), more preferentially 5-15%.
2. An additional, but optional component can be a support. The material can range from oxide supports like $ZrO_2$, $TiO_2$, MgO to conventional ones like $Al_2O_3$, $SiO_2$, activated carbon to zeolites, Rheney cobalt, cobalt derivatives, perovskites and clays. Supporting procedures can be simple mixing, impregnation, encapsulation or like.
3. An activation procedure is required for developing the final active state ready for the required syngas reaction. For oxide catalysts, an in situ reduction procedure in presence of $H_2$ containing gas for removing the oxygen and producing a metallic form of the catalyst; for carbides, in situ reduction procedure with a carburizing gas, like $CH_4$ or CO, which converts the metals into their carbides; for sulfides, in situ or ex situ reduction procedure with a sulfur rich gas, like $H_2S$, which converts the metals into their sulfides.

Continuing with FIG. 1, the syngas 100 that is provided to the reactor 80 can have varying ratios of $H_2$:CO of 0.7-4.0. The ratio decreases with the type of feedstock, which in descending order is methane, natural gas liquids, biomass, coal. The syngas is substantially free of impurities, but may contain $CO_2$, $N_2$ and $CH_4$. Depending on the type of MAS catalyst used, minor quantities of $H_2S$ could be acceptable.

The syngas 100 is passed through an intergas exchanger 110. Hot fluids, typically gas, exit the reactor 80 and provide the heat to the incoming syngas.

The heated syngas 120 is provided to the reactor 80 so as to flow through the catalyst-containing tubes 82 and participate in the MAS reaction, which reaction uses a Fisher-Tropsch synthesis related process to convert the syngas into mixed alcohols.

In addition to the syngas 120, a suitable solvent or liquid is introduced into the reactor, which may or may not participate in the MAS reaction. This additional injection can be one or more of the following:

Reactive supercritical fluids, which not only help in developing the supercritical phase but are also reactants themselves. They are preferentially converted into higher alcohols, but some conversion to unwanted lower alcohols and alkanes also takes place. These are methanol, ethanol, iso-propanol, n-propanol, either as pure liquids or a mixture thereof.

Recycled $CO_2$ which is a byproduct and exits the reactor. Some or all of the $CO_2$ can be recycled back to the reactor where it may or may not be activated into a reactant (depending upon the catalyst type selected), and may or may not be transformed into a supercritical fluid (SCF), depending upon the reactor operating conditions and the mole/volume % in the reacting gas.

Non-reactive solvents, which are higher molecular weight hydrocarbons, which remain as liquids in the reactor under the MAS conditions and transform the fixed bed reactor into a trickle bed reactor. Typically, decane, cetane, decahydronapthlene, various C11-20 hydrocarbons can be used as solvents. C11, or un-decane, is a component of gasoline, while C20, or eicosane, is found in lubricating oils, light waxes, etc. The remainder C12-C19 is in the range known in the oil industry as light waxes, lubricating oils, diesel or gasoil, kerosene and heavy gasoline. The product alcohols (for example $C_2$, $C_3$, etc.) are partially soluble in the non-reactive solvents. At room conditions (room temperature and pressure), the solvents are liquid. In the reactor, they remain liquid.

Non-reactive supercritical fluids (SCF), typically organic, of the likes of pentane, hexane, heptane, acetone, acetonitrile, etc. The fluids are transformed into the SCF phase only in the reactor under the preferred operating conditions for MAS (high temperature and pressure);

outside of the reactor they exist as liquids. For example, at room conditions, the fluids are liquid.

The above (reactive, non-reactive SCFs, non-reactive solvents and $CO_2$) can be used alone or in combination. For example, an additional control technique is to recycle a non-reactive SCF solvent which may have preferential solubility for some alcohols. When such a solvent is recycled, it carries with it dissolved amounts of product alcohols, which react with the syngas to make higher alcohols (i.e. they act as reactive SCF). The amount of alcohol solubility may be adjusted by the temperature and pressure of the vapor-liquid-liquid separator 175 (shown in FIG. 3 and discussed below) and/or by further separation options like distillation, adsorption, solvent extraction etc. As still another example, a non-reactive solvent or a non-reactive supercritical fluid, can be used with a reactive supercritical fluid such as methanol.

FIG. 1 shows the use of reactive supercritical fluids 310 and $CO_2$ 260 as injectants into the reactor 80 in addition to the syngas. The reactants are contacted with the catalyst through a gas-supercritical-solid phase. In a conventional process, where the reactor operates in a dry mode, with a gas-solid interface, the syngas interacts with the catalyst, reacts and the resulting product gas proceeds to the outlet. With the process described herein, the reactor operates in a "wet" mode. In the "wet mode" the supercritical fluid is made up of fine droplets in the stream. The droplets make the stream "wet" as opposed to "dry", where the wet stream has substantially more heat conductivity than the dry stream. The reactant gases first interact with the liquid, solvent or supercritical fluid, which then interacts with the catalyst as a mixed phase, reacts and the resulting product proceeds to the outlet of the reactor. The advantage of operating the reactor in a wet mode over a dry mode is that the mass and heat transfer are increased by many orders of magnitude over the catalyst surface, which results in greater product yields. Additionally, the heat transfer between the individual catalyst particles and from the catalyst to the reactor tube wall is improved, which improves the reactor stability and operability. The operating conditions of the reactor are 240-400 degrees C. and 500-2500 psi. Preferably, the operating temperatures are 280-360 degrees C. and pressures are 1200-1600 psi.

The products 150 of the reaction exit the reactor 80, pass through the exchanger 110 and then proceed on to a cooler 160. The reaction products, which are in plural phases, pass through the cooler 160 and are cooled to a temperature and/or pressure such that the mixed gas-supercritical fluid-liquid phase is broken down to a gas-liquid phase. The cooler 160 changes the phase conditions, or phase envelope, so that the reactor products, and any unreacted gases or solvent, can be separated.

The separation equipment includes a vapor-liquid separator 170 which receives the output of the cooler 160. The separator 170 separates the unreacted and byproduct gasses from the alcohol crude 210, which alcohol crude passes through a dryer 220. The dryer 220 removes small amounts of water 280 from the alcohol so as to avoid forming as azeotropes in the subsequent distillation. The dryer preferably has cycling (drying/regenerating) beds of a moisture absorbent material, such as aluminosilicate materials, clays, molecular sieves, zeolites, silicas, porous glasses, microporous charcoals, active carbons, or synthetic compounds. More preferentially they consist of molecular sieves of types 3A, 4A.

The alcohols exit the dryer 220 and enter a distillation column 230, where the light alcohols 310 are distilled off. The alcohol crude products 300 exit the distillation column 230. The light alcohols can be methanol ($C_1$) or a dominant distillate or a mixture of lower alcohols $C_1$-$C_3$. By selecting an appropriate column type (i.e. simple, dividing wall, complex) and by changing the operating column pressure, reboiler temperature and reflux ratios, the distillate composition can be varied. The distillation composition can also be altered through unit operations like azeotropic distillation, pervaporation and liquid-liquid extraction. This provides a great degree of freedom in achieving desired product crude alcohol (300) composition. This also provides flexibility to the whole system in light of changes in feedstock and syngas composition and/or $H_2$:CO ratios.

The light alcohols 310 are recycled back to the reactor 80. The lower alcohols, and in particular, methanol, reaches a reactive state over the catalyst and act as a reactant and not just a supercritical fluid medium.

Referring back to the separator 170, vapors 200 exit. The vapors include unreacted syngas, and inerts, as well as byproduct gases like $CO_2$ DME, methane, ethane, ethylene, propane, propylene, butane, iso-butane, etc. exit and are subsequently processed by passing through a chiller 230, a separator 240, and a $CO_2$ remover 250. $CO_2$ remover 250 can also be adjusted to remove unwanted sulfur compounds, like $H_2S$, COS, $CS_2$, $SO_x$ various mercaptans/thiols, thiophenes, disulfides from the recycle gas 260. $CO_2$ remover 250 has the capability of varying $CO_2$ and sulfide levels in the recycle stream 260 to levels required by the MAS reactor 80. The alkanes and other unwanted components are removed to avoid their buildup in the system. These can be flared and purged. The $CO_2$ and syngas 260 are recycled to the input of the syngas stream 100.

Figure 3:
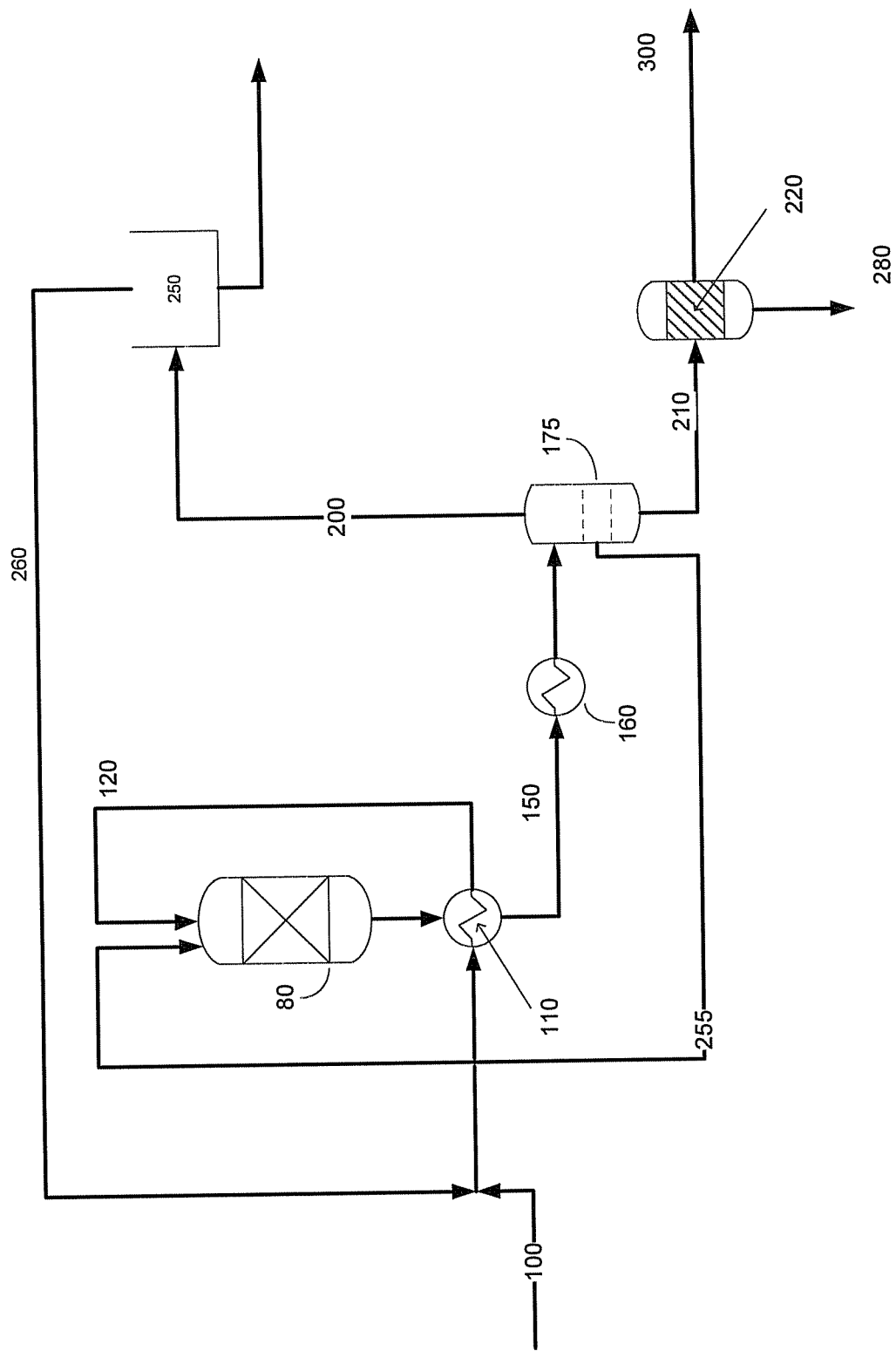
FIG. 3 is a schematic view of a system for practicing the MAS process, in accordance with still another embodiment.

FIG. 3 shows the injection of non-reactive solvent 255 into the reactor 80. The reaction products 150 pass through the exchanger 110 and the cooler 160. The solvents are recycled back into the reactor after being separated from the reaction products. The separator 175 is a vapor-liquid-liquid separator. The fluids exiting the cooler 160 are in a gas-liquid-liquid phase. The solvent has generally a lower density, compared to the alcohols in the separator and does not mix well with the alcohols. Consequently, the product alcohol 210 can be drained out of the bottom of the separator, while the lighter solvent 255 is taken off the top of the liquids, similar to decanting. The solvent 255 is recycled back to the reactor 80. $CO_2$ gas, unreacted syngas and lower alkanes 200 are removed from the separator 175. The alkanes and other unwanted components are removed in $CO_2$ remover 250. The $CO_2$ gas and unreacted syngas 260 are recycled back to the reactor 80. The unwanted components are removed from the $CO_2$ remover 250 and are flared and purged. The alcohol crude 210, removed from the separator 175, is passed through the dryer 220. The product alcohol crude 300 can be sent to a distillation column if further separation is desired.

The use of non-reactive solvents alters the flow regime in the reactor. This in turn leads to improvement in the heat transfer and mass transfer.

Figure 4:
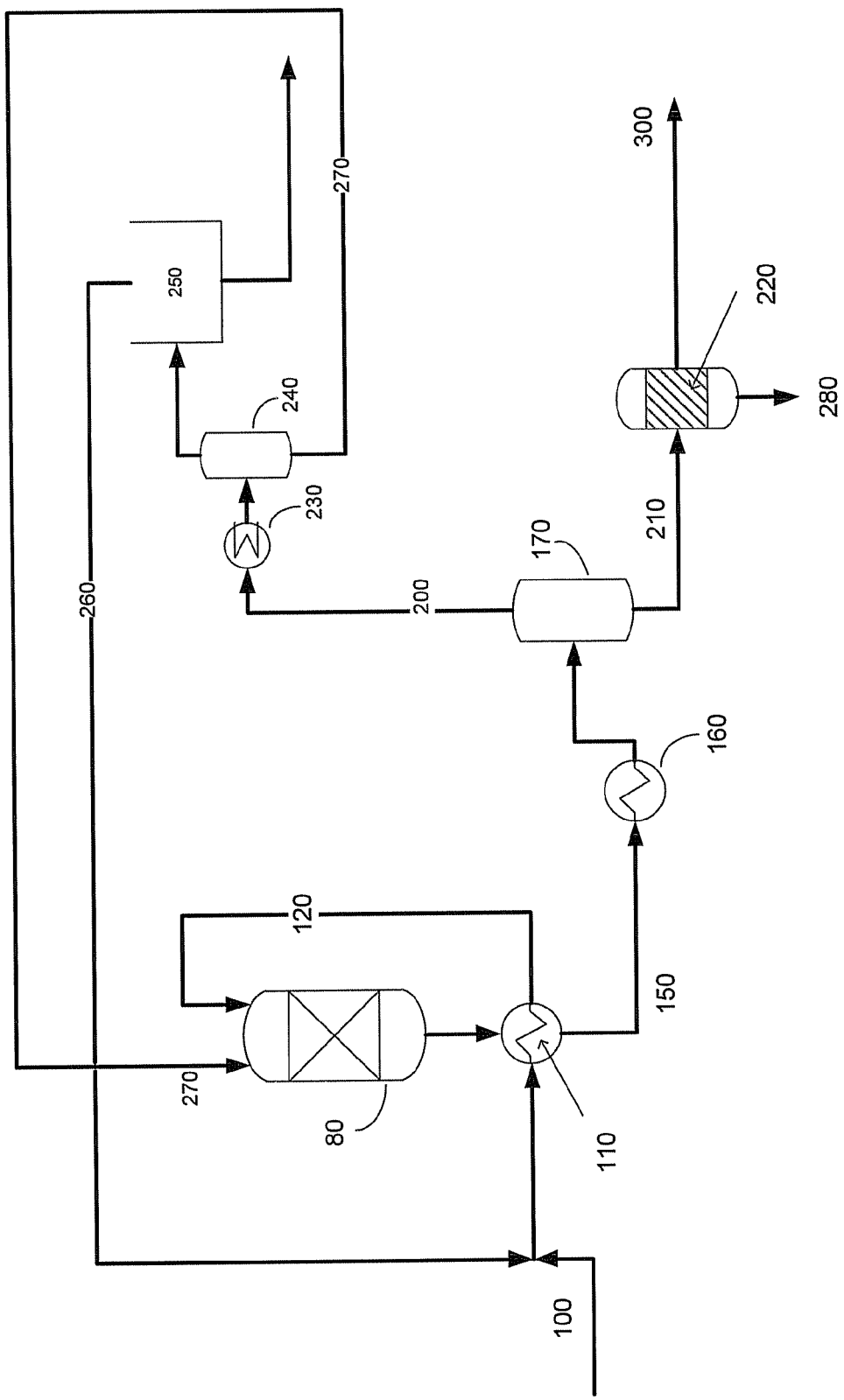
FIG. 4 is a schematic view of a system for practicing the MAS process, in accordance with still another embodiment.

FIG. 4 shows still another embodiment which uses a non-reactive supercritical fluid as a recycle component. The system is substantially the same as shown in FIG. 1, except that the separator 240 separates $CO_2$ from the non-reactive supercritical fluid. Outside the reactor 80, the non-reactive supercritical fluid exists as a liquid. The $CO_2$ is further purified in a removal section and returned to the syngas stream to inject into the reactor. The non-reactive supercritical fluids 270 are recycled to the reactor as well.

The use of a non-reactive supercritical fluid also alters the flow regime in the reactor. This in turn leads to improvement in the heat transfer and possibly mass transfer as well.

The non-reactive solvents and non-reactive supercritical fluids are initially added to the process on startup or soon thereafter. By recovering the non-reactive components, they can be reused in the reactor 80. Any non-reactive fluids that are lost and unrecovered are made up by adding more fluid to the process.

When the non-reactive solvents or the non-reactive supercritical fluids are added to the syngas, the mixture is turned into a supercritical mixture, and the process operates in a wet mode.

The mixed alcohols produced are $C_1$-$C_{10}$. By providing the recycle components, the MAS reaction in the reactor is controlled and stabilized. In addition, greater yields of higher alcohols can be achieved because the reaction can be operated at higher temperatures and pressures than are available with the prior art. Furthermore, by recycling $CO_2$, the carbon emissions by the MAS processor are reduced.

The MAS process is flexible in that fluctuations in syngas ratios of $H_2$:CO can be accommodated. If the syngas ratio changes, as in for example due to a new source of syngas, then the recycle components can be adjusted to achieve optimum mixed alcohol production.

Examples will now be discussed. In the examples that follow, reactor pressures are 1500 psi and space velocity of the fluids through the catalyst 3000 L/Kg/hr. Temperatures are 320-350 degrees C. Because the temperature profile can vary over the length of the catalyst bed, a single catalyst bed temperature does not present a full picture of temperatures. Instead, it has been found that a weighted averaged bed temperature (WABT) is suitable. The WABT is determined from thermocouples 92 covering the majority of the catalyst bed. In addition to WABT, bed peak temperature at stable operation is useful.

Two test regimes were used. One regime (A) used a single tubular reactor. The other regime (B) used two tubular reactors scaled up from regime (A).

Regime (A)

A 92-gram (g) sample of pelletized catalyst (3-millimeter [mm]×1-mm cylindrical pellets) was loaded in a reactor according to the packing diagram illustrated as FIG. 2. Note the spaced thermocouple positioning within the catalyst bed as specified in the Figure. The lower two thermocouples cover 80% of the bed. The bulk density of the catalyst was determined to be 1.32 g/cubic centimeter (cc). The catalyst was packed into a 24-inch-long, 0.75-inch-outside diameter (o.d.) stainless steel tubular reactor. The catalyst was supported by stainless steel frits and glass beads. In order to prevent the generation of exotherms during heat-up of the fresh catalyst, syngas diluted with nitrogen was used to initiate catalyst activation. Two mass flow controllers were used to vary the composition of syngas and nitrogen mixture. In a typical test, mass flow controllers are used to introduce the syngas into the reactor at the desired flow rate. 4 vol % nitrogen added to every feed gas mixture serves as internal standard. The system was tested through an exhaustive set of operating conditions, in which temperature, pressure, syngas ratio and reactant space hourly velocity was varied. Moreover, a number of solvents were tested to improve reactor stability and recycle of product methanol and/or $CO_2$ was also tested.

Every hour liquid products were collected from two condensing pots, maintained at 0 degrees C. and −5 degrees C. respectively. The weight of the product was recorded on hourly basis. Online LGA and GC analysis of the gaseous product was performed hourly, and total volumes of feed gas and product gas were also recorded hourly. Liquid product samples (1 g) were mixed with 100 milligram (mg) of 2-methyl-1-butanol internal standard, and the mixture was analyzed by calibrated gas chromatography-mass spectrometry (GC-MS).

Regime (B)

A pilot scale reactor system was filled with ~1 kg of the same catalyst tested in Regime (A) above. The system consists of two identically sized reactors of 63-inch length and 1-inch o.d. Both reactors were packed with an equal volume of catalyst and connected in parallel. The product streams emerging from the two reactors were combined and removed from the reactors using a single stainless steel tube. Provisions were made to introduce nitrogen within the reactor and the outer heating assembly to control any possible exotherms. Every feed gas was analyzed with the LGA before use. Based on the composition of the gases needed for the tests, hydrogen, carbon monoxide, and nitrogen were mixed in appropriate ratios using mass flow controllers to obtain a feed syngas consisting of carbon monoxide and hydrogen, with 4 vol % nitrogen added to every feed gas mixture to serve as internal standard.

Liquid products were collected from two condensing pots every hour and the weight of the product was recorded. The total volume of the feed gas and product gas were also recorded hourly. An accurate mass balance was obtained for each test based on carbon monoxide input and conversion to products.

The test results will now be discussed. Regime (A) has A1, A2, A3, and A4, while regime (B) has B1 and B2, in which a separate process control experiment is outlined.

[A1] Effect of Solvents on Reactor Performance

When in the dry mode, there is a limitation in the temperature that can be achieved. This limits the mixed alcohol synthesis, since it is known to those experienced in the art, that at higher temperatures, increased alcohol productivity is possible, but more importantly, the distribution within the alcohol crude is favored for alcohols higher than methanol.

With the use of liquid addition, a significant impact is seen on the temperature profile through the reactor. This is an indication that with the use of non-reactive solvents, the catalyst bed is efficiently utilized.

In Table 1 below it is shown that, while operating in the temperature range of 300-400 degrees C., preferentially between 320 and 350 degrees C., for stable reactor operation the peak temperature of the reactor bed can, with the injection of a non-reactive liquid, be increased from 325 to 347 degrees C. (table column 1, 2 and 3). Injection of a reactive liquid, like methanol, does not only allow stable operation at increased peak temperature, it also shifts the product distribution to higher alcohols (table column 4 and 5 give data for the raw reactor effluent and net reactor production composition). Addition of $CO_2$ to the methanol injection only further enhances the product improvements (see table, column 6 and 7, for raw and net data, respectively).

TABLE 1

| | | | | | | | A1-6 | |
| | | | | | A1-4 | A1-5 | 4% MeOH + | A1-7 |
| | | | A1-2 | | methanol | adjusted | 5% CO2 | adjusted |
| | | A1-1 | Hexane | A1-3 | @4%, | methanol | inlet, | 4% MeOH + |
| | | Dry | @ 5% | dodecane | unadjusted | @4% | unadjusted | 5% CO2 |
| | | run | inlet | @5% inlet | MeOH | inlet | methanol | inlet |
| | H2/CO | 1 | 1 | 1 | 1 | 1 | 1 | 1 |
| Solvent injected | ml/min | X | 1.67 | 2.45 | 0.31 | 0.31 | 0.31 | 0.31 |

TABLE 1-continued

| | | Example No. | | | | | | |
|---|---|---|---|---|---|---|---|---|
| | | A1-1 Dry run | A1-2 Hexane @ 5% inlet | A1-3 dodecane @5% inlet | A1-4 methanol @4%, unadjusted MeOH | A1-5 adjusted methanol @4% inlet | A1-6 4% MeOH + 5% CO2 inlet, unadjusted methanol | A1-7 adjusted 4% MeOH + 5% CO2 inlet |
| CO2 injected | % of inlet | X | X | X | X | X | 5 | 5 |
| Conversion | CO % | 27.7 | 23.2 | 22.8 | 20.9 | 20.9 | 24.9 | 24.9 |
| STY (g/kgcat/h) | alcohols | 0.135 | 0.213 | 0.158 | 0.262 | 0.186 | 0.227 | 0.151 |
| | C2+/C1 | 1.0 | 1.2 | 1.0 | 2.0 | 19.2 | 3.1 | 195.4 |
| | | Reactor Effluent Material balance (wt %) | | | | | | |
| Gas Composition (vol %) | CO | 45.4 | 44.6 | 44.9 | 44.5 | 44.5 | 40 | 40.0 |
| | CO2 | 3.0 | 4.0 | 4.3 | 4.6 | 4.6 | 8.9 | 8.9 |
| | H2 | 43.1 | 41.4 | 42.0 | 42.8 | 42.8 | 40.1 | 40.1 |
| | N2 | 5.2 | 4.7 | 4.8 | 4.6 | 4.6 | 4.7 | 4.7 |
| | Methane | 0.9 | 1.2 | 1.3 | 1.4 | 1.4 | 1.1 | 1.1 |
| | C2 + alkanes | 0.5 | 1.2 | 0.4 | 0.4 | 0.4 | 0.5 | 0.5 |
| Liquid Composition (wt %) | Methanol | 47.7 | 45.1 | 49.5 | 32.6 | 4.8 | 24.1 | 0.5 |
| | Ethanol | 34.3 | 36.5 | 32.1 | 51.2 | 72.3 | 54.7 | 71.2 |
| | Propanols | 10.3 | 13.1 | 12.9 | 12.2 | 17.2 | 15.5 | 19.9 |
| | Butanols | 2.4 | 2.8 | 2.6 | 2 | 2.8 | 4.2 | 6.6 |
| | Pentanols | | 0 | | 0 | 0 | | 0 |
| | others | 5.3 | 2.5 | 2.9 | 2 | 2.8 | 1.4 | 1.8 |
| Bed peak Temp, oC | temp | 325 | 347 | 346 | 351 | 351 | 349 | 349 c |

The adjusted results of the reactive alcohol and alcohol/$CO_2$ injection are derived according to the following convention: The amount of alcohols that is added as the reactive SCF, is subtracted from the final product alcohol crude, and the overall composition is adjusted accordingly (examples A1-5 and A1-7 instead of A1-4 and A1-6). Physically, this is represented in FIG. 1, where the reactive SCF is removed from the alcohol crude by distillation and is recycled back to the system. This is represented by examples A1-5 and A1-7, where methanol is the reactive SCF and the product alcohol crude composition and yield has a corresponding amount of this solvent subtracted from it.

Examples A1-2 and A1-3 use non-reactive components, which are supercritical.

Figure 5:
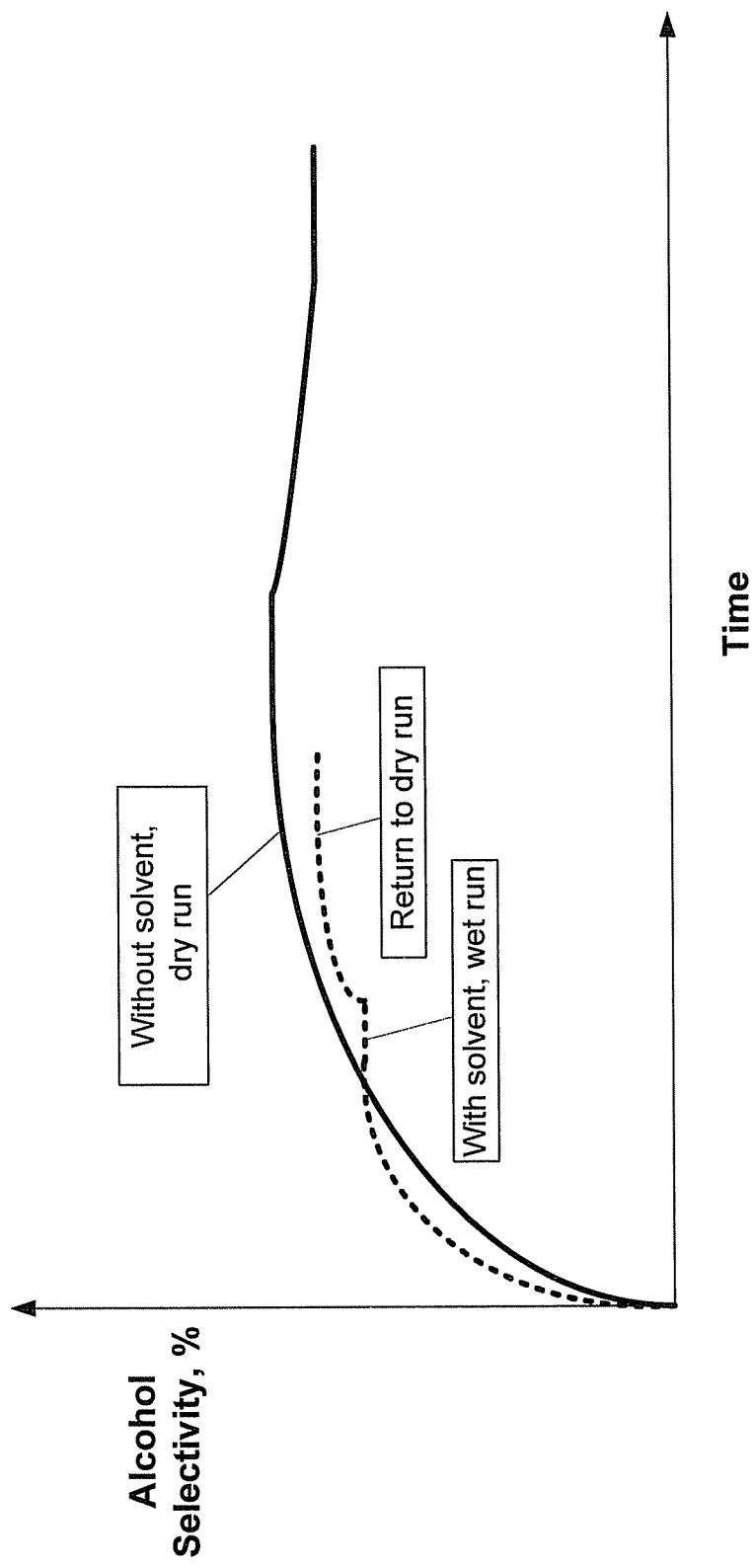
FIG. 5 is a graph showing the accelerated development of final steady state alcohol selectively.

[B1] It is well recognized by those skilled in the art that for MAS catalysts there is a certain set-in period required. The catalyst develops the required steady state activity after some hours under a syngas environment and then somewhat declines to reach a final steady state. This example demonstrates how the final steady state of the catalyst can be achieved in an expedited manner by use of a reactive SCF, namely methanol, qualitatively represented by FIG. 5. The advantage is that before the use of a SCF solvent, weighted average bed temperatures higher than 325 degrees C. were not achievable as the catalyst had not reached a stable final condition, but after the activation period with the reactive SCF, the catalyst achieves its final steady state and can be operated at a WABT as high as 355 degrees C. without a solvent. Table 2 shows the results.

TABLE 2

| Example | WABT, oC | Press, psi | SV, L/kg/hr | H2:CO | Conv, % | Alc yield, g/kgcat/hr | MeOH % | EtOH % | PrOH % | BuOH % |
|---|---|---|---|---|---|---|---|---|---|---|
| B1-1 | 325 | 1500 | 3000 | 1 | 18 | .12 | 61.6 | 27.4 | 7.7 | 2.0 |
| B1-2‡ | 355 | 1500 | 3000 | 1 | 27 | .12 | 52.6 | 29.0 | 12.2 | 2.9 |

‡Reactor run in dry mode after 24 hours of operation with 5% methanol (reactive SCF) at reactor inlet under similar operating conditions Even though the example uses methanol, the same results can be achieved by using non-reactive supercritical fluids.

[A2] This example, operating in the temperature range of 300-400 degrees C., preferentially between 320 and 350 degrees C., demonstrates that by using methanol as a reactive SCF, greater quantities of higher alcohols are obtained. As described above, for the methanol recycle case A2-2, the alcohol yield and alcohol composition are presented after subtraction of methanol amount that corresponds to what was injected into the reactor. Table 3 shows the results.

TABLE 3

| Example | Press, psi | SV, L/kg/hr | $H_2$:CO | Conv, % | Alc yield, g/kgcat/hr | MeOH % | EtOH % | PrOH % | BuOH % |
|---|---|---|---|---|---|---|---|---|---|
| A2-1 | 1500 | 3000 | 1 | 30 | 0.18 | 45 | 39 | 11 | 2 |
| A2-2* | 1500 | 3000 | 1 | 21 | 0.18 | 5 | 72 | 17 | 3 |

*With alcohol injection, results in 77% more higher alcohol

[A3] Depending upon the operating conditions, specific cuts within the alcohol crude product can be targeted. This offers great flexibility to the whole process whereby changing the operating conditions, product alcohol composition can be tailored to market demand. In examples A3-1 and A3-2, operating in the temperature range of 300-400 degrees C., preferentially between 320 and 350 degrees C., a high concentration of butanols is achieved by recycling a reactive SCF mix of light alcohols. The butanols may be composed of n-butanol, isobutanol, sec-butanol or tert-butanol or any mixture of thereof, but the major components are usually n-butanol and iso-butanol (or 2-methyl-1-propanol). The light alcohol mix used is methanol/ethanol/propanols, where methanol, ethanol, or propanol can vary between 0-40% vol. In this particular example a mixture of methanol/ethanol/propanol of 40/40/20 vol % has been used. This light alcohol mix is obtained from a separation operation like distillation which can extract a light alcohol mix from the product alcohol crude with ease and is recycled back to the reactor. In A1-7, equally well operating in the temperature range of 300-400 degrees C., preferentially between 320 and 350 degrees C., ethanol is the major component, and the reactive SCF is rich in methanol, but can contain ethanol, propanol, methyl acetate and ethyl acetate. Table 4 shows the results.

TABLE 4

| | | Example No. | | |
|---|---|---|---|---|
| | | A1-7 4% MeOH+ 5% CO2 inlet | A3-1 3.7% alcohol mix @ inlet | A3-2 7.5% alcohol mix @ inlet |
| Pressure | Psi | 1500 | 1500 | 1500 |
| Space velocity | L/kg/hr | 3000 | 3000 | 3000 |
| | $H_2$/CO | 1 | 1 | 1 |
| Solvent injected | ml/min | 0.31 | 0.42 | 0.84 |
| $CO_2$ injected | % of inlet | 5 | X | X |
| Conversion | CO % | 24.9 | 24.8 | 25.8 |
| Yield (g/gcat/h) | Alcohols | 0.15 | 0.11 | 0.21 |
| | C2+/C1 | 195.40 | 1.2 | 4.8 |
| Material balance (wt %) | | | | |
| Gas Composition (vol %) | CO | 40.0 | 43.1 | 40.8 |
| | $CO_2$ | 8.9 | 5.39 | 6.44 |
| | $H_2$ | 40.1 | 43.4 | 43.2 |
| | $N_2$ | 4.7 | 4.69 | 4.5 |
| | Methane | 1.1 | 1.61 | 1.94 |
| | C2 + alkanes | 0.5 | 1.5 | 2.1 |
| Liquid Composition (wt %) | Methanol | 0.5 | 36.2 | 14.7 |
| | Ethanol | 71.2 | 4.9 | 0 |
| | Propanols | 19.9 | 12.7 | 15 |
| | Butanols | 6.6 | 21.6 | 54.4 |
| | Pentanols | 0 | 2.6 | 1.7 |
| | Others | 1.8 | 22.0 | 14.2 |

[A4] In this example it is demonstrated how to take advantage of varying syngas ratios. All runs are operating in the temperature range of 300-400 degrees C., preferentially between 320 and 350 degrees C. Run A4-2 uses a $H_2$:CO ratio of 2, which results in an alcohol crude with high content of methanol. Separating part of the methanol from this product crude, and introducing it back into the reactor as a reactive SCF, changes the product alcohol composition. Note that a product composition obtained in A4-1 is more suited to use as a fuel or as a fuel additive, as outlined in U.S. Pat. No. 7,559,961. Table 5 shows the results.

TABLE 5

| | | Example | | |
|---|---|---|---|---|
| | | A2-2 | A4-1 | A4-2 |
| Pressure | psi | 1500 | 1500 | 1500 |
| Space velocity | L/kg/hr | 3000 | 3000 | 3000 |
| | $H_2$/CO | 1 | 2 | 2 |
| CO conversion, % | | 21 | 36 | 35 |
| Solvent injected | ml/min | 0.31 | 0.31 | X |
| Alcohol Selectivity, % | | 66 | 58 | 73 |
| Alcohol yield, g/kgcat/hr | | 0.19 | 0.20 | 0.23 |
| Liquid Composition, wt % | Methanol | 5 | 15 | 59 |
| | Ethanol | 72 | 61 | 31 |
| | Propanols | 17 | 15 | 7 |
| | Butanols | 3 | 4 | 2 |

[B2] Referring to FIG. 6, this example, operating in the temperature range of 300-400 degrees C., preferentially between 320 and 350 degrees C., demonstrates that by using methanol as a reactive SCF, the operability of a MAS reactor under temperature run-away conditions can be regained. Operating at a temperature of 350 degrees C. the reactors of configuration B moved from stable operation into a temperature run away, caused by a local hot spot in reactor. The reactor temperatures started to increase and approach 400 degrees C. In order to regain control in first instance the hydrogen supply to the reactor was reduced, hence, effecting one of the reactants of the methanation reaction. The resultant effect was a slower increase of the reactor temperatures. Subsequently the methanol injection was initiated, resulting in an immediate reversal of the temperature behavior and stable operation at 350 degrees C. would be resumed.

The foregoing disclosure and showings made in the drawings are merely illustrative of the principles of this invention and are not to be interpreted in a limiting sense.

The invention claimed is:

1. A method for producing alcohols from syngas, comprising the steps of:
    a) providing a catalyst in a mixed alcohol synthesis reactor, wherein the catalyst is retained in the reactor during operation of the reactor;
    b) providing syngas to the reactor, the reactor operating in a temperature range of 240-400 degrees C. and at pressures of 500-2500 psi, and contacting the syngas with the catalyst in the presence of liquid non-reacting components, wherein reaction products are formed, the reaction products comprising mixed alcohols;
    c) removing at least a portion of the reaction products from the reactor, while retaining the catalyst in the reactor;
    d) removing liquid non-reactive components from the mixed alcohols of the reaction products;

e) maintaining the temperature in the reactor in the temperature range by reintroducing at least part of the liquid non-reactive components into the reactor and interacting the syngas with the reintroduced liquid non-reactive components and with the catalyst in a trickle bed mode so as to produce further reaction products that comprise mixed alcohols, wherein the liquid non-reactive components are solvents selected from the group consisting of decane, cetane, decahydronapthalene and C11-C20 hydrocarbons.

2. The method of claim 1, wherein the reintroduced liquid solvent non-reactive components alter the flow regime within the reactor and improve heat transfer and mass transfer.

3. The method of claim 2, wherein the step of removing liquid non-reactive components from the mixed alcohols further comprises the step of using a vapor-liquid-liquid separator.

4. A method for producing alcohols from syngas, comprising the steps of:
 a) providing a catalyst in a mixed alcohol synthesis reactor, wherein the catalyst is retained in the reactor during operation of the reactor;
 b) providing syngas to the reactor, the reactor operating in a temperature range of 240-400 degrees C. and at pressures of 500-2500 psi, and contacting the syngas with the catalyst in the presence of non-reacting components, wherein reaction products are formed, the reaction products comprising mixed alcohols;
 c) removing at least a portion of the reaction products from the reactor, while retaining the catalyst in the reactor;
 d) removing non-reactive components from the mixed alcohols of the reaction products;
 e) maintaining the temperature in the reactor in the temperature range by reintroducing at least part of the non-reactive components into the reactor and interacting the syngas with the reintroduced non-reactive components and with the catalyst in a wet mode so as to produce further reaction products that comprise mixed alcohols, wherein the reintroduced non-reactive components are liquid at standard room temperature and pressure and which non-reactive components are supercritical in the reactor, wherein the supercritical fluid is selected from the group consisting of pentane, hexane, heptane, acetone, and acetonitrile.

5. The method of claim 4, wherein the reaction products comprise $CO_2$, wherein the step of removing non-reactive components from the mixed alcohols further comprises using a first vapor-liquid separator to separate unreacted syngas, $CO_2$ and the non-reactive components from the mixed alcohols, and then a second separator to separate the non-reactive components from the unreacted syngas and $CO_2$.

6. The method of claim 1, wherein the step of providing syngas to the reactor further comprises the step of providing syngas in the range of 0.07-4.0 of $H_2:CO$.

7. The method of claim 1, wherein the step of providing syngas to the reactor farther comprises passing the syngas and the liquid non-reactive components through a first permeable barrier, then contacting the syngas with the catalyst to form reaction products and passing the reaction products and the liquid non-reactive components through a second permeable barrier, while, retaining the catalyst in an upstream location from the second percale barrier.

8. The method of claim 1, wherein the reactor operates in the temperature range of 280-360 degrees C.

9. The method of claim 4, wherein the step of providing syngas to the reactor further comprises the step of providing syngas in the range of 0.07-4.0 of $H_2:CO$.

10. The method of claim 4, wherein the step of providing syngas to the reactor further comprises passing the syngas and the non-reactive components through a first permeable barrier, then contacting the syngas with the catalyst to form reaction products and passing the reaction products and the non-reactive components through a second permeable barrier, while retaining the catalyst in an upstream location from the second permeable harrier.

11. The method of claim 4, wherein the reactor operates in the temperature range of 280-360 degrees C.

* * * * *